(12) United States Patent
Goetzinger et al.

(10) Patent No.: US 6,497,820 B1
(45) Date of Patent: *Dec. 24, 2002

(54) RAPID METHOD FOR SEPARATION OF SMALL MOLECULES USING REVERSE PHASE HIGH PERFORMANCE LIQUID CHROMATOGRAPHY

(75) Inventors: Wolfgang K. Goetzinger, Boston, MA (US); James N. Kyranos, Wollaston, MA (US)

(73) Assignee: ArQule, Inc., Woburn, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/600,686

(22) PCT Filed: Feb. 3, 1999

(86) PCT No.: PCT/US99/02371

§ 371 (c)(1),
(2), (4) Date: Sep. 12, 2000

(87) PCT Pub. No.: WO99/39195

PCT Pub. Date: Aug. 5, 1999

Related U.S. Application Data (60) Provisional application No. 60/073,489, filed on Feb. 3, 1998.

(51) Int. Cl.[7] .............................................. B01D 15/08
(52) U.S. Cl. ..................... 210/635; 210/656; 210/198.2
(58) Field of Search .................. 210/635, 656, 210/659, 143, 198.2; 95/82; 96/101

(56) References Cited

U.S. PATENT DOCUMENTS

| | | | |
|---|---|---|---|
| 4,187,177 A | 2/1980 | Stahl | 210/198 |
| 4,732,687 A | 3/1988 | Müller et al. | 210/656 |
| 4,737,292 A | 4/1988 | Ritacco et al. | 210/656 |
| 4,762,617 A | 8/1988 | Stevens | 210/635 |
| 4,828,695 A | 5/1989 | Yamamura et al. | 210/198.2 |
| 4,909,941 A | 3/1990 | Poll et al. | 210/635 |
| 5,135,650 A | 8/1992 | Hierten et al. | 210/198.2 |
| 5,510,240 A | 4/1996 | Lam | 435/7.1 |
| 5,646,285 A | 7/1997 | Baindur et al. | 546/298 |
| 5,670,054 A | 9/1997 | Kibbey et al. | 210/656 |
| 5,683,899 A | 11/1997 | Stuart | 435/172.2 |
| 5,693,223 A | 12/1997 | Yamada | 210/198.2 |
| 5,712,171 A | 1/1998 | Zambias | 436/518 |
| 5,968,361 A | * 10/1999 | Goetzinger | 210/635 |

FOREIGN PATENT DOCUMENTS

| | | | |
|---|---|---|---|
| WO | WO95/18627 | 7/1995 | 210/656 |
| WO | WO95/18972 | 7/1995 | 210/656 |
| WO | WO96/31263 | 10/1995 | 210/656 |
| WO | WO96/22529 | 7/1996 | 210/656 |

OTHER PUBLICATIONS

Dwyer et al., "High Speed Liquid Chromatography: A Review", *J. Liq. Chrom.*, (1987), 10:8&9:1769–1787.

Engelhardt et al., "Chromatographic . . . reversed phases", *Journal of Chromatography*, (1991), 544:371–379.

Engelhardt et al., "High–performance . . . 1.5 μm particles", *American Laboratory*, (Apr. 1998), 40–44.

Gant et al., "Practical Benefits of High Speed . . . Analysis", pp. 1–8 (Undated).

Jones Chromatography, "Lighting™ —Harness the Power", Brochure, pp. 1–5 (Undated).

Mac Mod Forum, (1997), vol. 29, pp. 1–8 (Undated).

Miller, C. et al., "Peptide Chemistry: . . . Zone Electrophoresis", *Biopolymers*, (1996), 40:265–317.

Van Der Wal et al., "Performance of . . . Chromatography", *Analytical Biochemistry*, (1980), 105:219–229.

Weller et al., "High throughput . . . parallel synthesis", *Molecular Diversity*, (1997), 3:61–70.

YMC, Inc., "CombiChrom™ HPLC Columns", Brochure, pp. 1–2 (Undated).

* cited by examiner

*Primary Examiner*—Ernest G. Therkorn
(74) *Attorney, Agent, or Firm*—Wolf, Greenfield & Sacks, P.C.

(57) ABSTRACT

Disclosed is a rapid method for the separation of small organic compounds using gradient reverse phase HPLC. The method achieves a run time of one minute or less and a resolution with a peak production of at least 1 peak/2 seconds. The method is also able to achieve the separation of a compound from a mixture of compounds in an elution sample having a volume of 2 milliliters of less.

34 Claims, 7 Drawing Sheets

RAPID METHOD FOR SEPARATION OF SMALL MOLECULES USING REVERSE PHASE HIGH PERFORMANCE LIQUID CHROMATOGRAPHY

REFERENCE TO RELATED APPLICATIONS

This application is a 371 of PCT/US99/02371 filed Feb. 3, 1999, which, in turn, claims the benefit of U.S. application Ser. No. 09/028,401, filed Feb. 24, 1998, now U.S. Pat. No. 5,968,361, and claims the benefit of U.S. Provisional Application No. 60/073,489, filed Feb. 3, 1998.

FIELD OF THE INVENTION

The invention relates to the field of high performance liquid chromatography and more particularly to the field of high performance liquid chromatography separation of small organic molecules.

BACKGROUND OF THE INVENTION

High-performance liquid chromatography (HPLC) is commonly used for analytical and preparative separations of biopolymers and other organic molecules. For instance, the individual components within a complex organic reaction mixture may be separated by HPLC. HPLC is performed in a pressure-resistant tube containing a stationary adsorbent which is the packing material. A pressure mechanism exerts pressure on a mobile phase applied to one end of the column and moves it through the column causing it to exit the opposite end of the column. A sample containing a mixture of compounds is injected onto the column through a sample injection port. As the sample moves through the packing material, the various components of the sample adsorb to the packing material with different affinities. The components, therefore, can elute from the column separately under appropriate conditions. On a reverse phase HPLC column the compounds within a sample are separated based on hydrophobicity.

HPLC analysis may be performed in isocratic or gradient mode. An isocratic HPLC separation is one which is carried out under a constant eluant composition. A gradient HPLC separation is characterized by a gradual change in the percentage of two or more solvents applied to the column over time. The change in solvent often is controlled by a mixing device which mixes solvent A and solvent B to produce the HPLC solvent just prior to its movement through the column. The amount of time over which the gradient is changed from one extreme to the opposite extreme is the gradient time.

Generally in gradient chromatography it is believed that increasing the flow rate and/or decreasing the gradient time results in a loss of resolution, that is the ability of the column to separate the components within the mixture into discrete eluant fractions. (Snyder, L., et al., "Practical HPLC Method Development", *Wiley-Interscience Publication*, (1997).

Rapid methods for the preparation and isolation of potential drug candidates using automated synthetic organic chemistry techniques to create combinatorial libraries represents an important advance in drug discovery. Certain combinatorial libraries encompass a series of compounds having common structural features but which differ in the number or type of group attached to the main structure. Each compound within a combinatorial library created by parallel synthesis is a separate sample housed in a tube or well of a microtitre plate. Once the library is completed, each sample is subjected to quality control analysis to confirm that the particular sample includes the desired library component at the requisite purity. Generally this is accomplished by subjecting the samples to HPLC with UV, evaporative light scatter detection (ESLD), or mass spectrometry detection; IR; NMR; or any other appropriate analytical techniques. The qualitative analysis of such combinatorial libraries by conventional HPLC requires on the average 5 to 20 minutes in order to separate various compounds within the sample.

A problem encountered with prior art methods for separation of compounds in combinatorial libraries using HPLC is the length of time required for separation of each sample. Each sample of a combinatorial library produced by parallel synthesis must be analyzed separately to determine if that sample houses the appropriate compound and/or to separate the compounds in the mixture. Each library includes thousands of samples each of which require an average run time of 10 minutes. The amount of time required to perform separations on these samples may run on the order of months using standard equipment and methodology.

SUMMARY OF THE INVENTION

The present invention provides rapid methods for the analysis and preparative isolation of relatively simple synthetic mixtures containing a small number of reagents, the product(s) of interest and a relatively small number of side products using HPLC. The methods of the invention reduce the HPLC analysis run time per sample from an average of 5–20 minutes shown in the prior art (Weller, et al., *Molecular Diversity*, (1997), 3:61–70) to less than one minute without a meaningful loss of resolution. The invention depends in part upon the discovery that small organic molecules could be separated on a full gradient reverse phase HPLC by minimizing the total volume of eluant applied to the column, maximizing the linear flow velocity of the eluant and compressing the gradient time to resolve a peak at least every 2 seconds. A full gradient is defined as a change in the solvent B concentration of at least 50%. For example, if the initial concentration of solvent B was 15%, a full gradient would be achieved when the concentration of solvent B reached 65%. The prior art believed that if the total eluant volume was decreased and the flow rate increased to the levels indicated in the invention, the resolution of the peaks eluting off the column would be significantly decreased to an extent that it would not be possible to obtain a discrete separation of a mixture of small organic compounds.

The methods of the invention include applying a mixture of compounds to a reverse phase column configured in a gradient high performance liquid chromatography system, and operating with a flow rate of at least 5 column volumes/min. A complete gradient is applied to the column at a rate which uses a maximum total volume of 10 column volumes; preferably 5 column volumes in order to maximize speed. These parameters allow each small organic component within the mixture of compounds to elute in a distinct fraction from the column with sufficient resolution which permits a peak production of at least 1 peak/2 seconds. A one minute analysis, using a peak production of 1 peak/2 seconds, would translate into an analysis which could baseline separate more than 30 individual peaks.

The amount of time that the complete separation requires depends on the parameters used in the separation, such as the length of the column and the amount of solvent used. Preferably the mixture of compounds is applied to the column at a first time point and all the compounds are eluted within a time period of less than one minute from the first time point. In other preferred embodiments all compounds are eluted within a time period of less than 30 seconds. In other embodiments all compounds are eluted within a time period of less than 20 seconds.

In one embodiment of the invention the method also includes the step of detecting at least one of the compounds as it elutes from the column. In another embodiment the method includes the step of collecting at least one of the compounds in a distinct fraction as it elutes from the column.

In preferred embodiments, the mixture of molecules includes reactants and a substantially pure product of the reactants.

In other preferred embodiments, including those listed above, the column is less than or equal to 30 mm in length. The column is less than or equal to 15 mm in length in other embodiments.

According to other preferred embodiments, including those listed above, the column has a packing material which has an average diameter of less than 5 microns.

In other preferred embodiments, including those listed above, the peak production is at least 1 peak/1 second. The peak production is at least 1 peak/0.5 seconds in other embodiments.

Preferably the total volume of liquid applied to the column per analysis is less than 15× column volumes, preferably less than 8× column volumes. The total volume of liquid may include a cleaning volume having a maximum of 2× column volume. In a preferred embodiment the total volume of liquid may include an equilibration volume having a maximum of 1× column volume.

In other embodiments, including those listed above, the mixture of molecules is a member of a combinatorial library of small organic molecules. Preferably the combinatorial library is made by means of parallel synthesis methods and the method is performed for high throughput purification and/or quality control analysis.

In additional embodiments the column flow rate has a linear velocity of at least 3 mm/sec. In another embodiment the linear velocity is 5 mm/sec.

The small organic compounds which elute from the column are typically analyzed by a detection device such as a UV detector. In one embodiment of the invention the small organic molecules are analyzed by both a UV detector and a mass spectrometer.

In one embodiment the method is a method for analysis of at least one compound in the mixture of compounds. Preferably less than 10 μg of the mixture of compounds is applied to the column for the analysis. In an embodiment the sample of compounds is not collected for further use after it is eluted from the column.

In another embodiment the method is a method for preparative isolation of at least one compound in the mixture of compounds. Preferably between 1 and 100 mg of the mixture of compounds is applied to the column for the analysis. In an embodiment the compounds are collected in separate fractions for further use after they are eluted from the column. Preferably the at least one compound is collected in a fraction having a volume of 2 milliliters or less.

The high performance liquid chromatography may be performed at a temperature of greater than 20° C. in one embodiment. In another embodiment the method is performed at a temperature of greater than 50° C. In a preferred embodiment the method is performed at a temperature of greater than 60° C.

In another aspect the invention is a rapid high performance liquid chromatography method for the preparative isolation of a concentrated fraction of a small organic compound from a mixture of compounds. The method includes the steps of applying the mixture of compounds to a reverse phase column in a gradient high performance liquid chromatography system, wherein the column has a flow rate of at least 5 column volumes/min, applying a complete gradient to the column in a maximum volume of 10× column volume, causing the small organic compound to elute in a distinct fraction, separate from the other molecules, from the column such that the elution permits resolution with a peak production of at least 1 peak/4 seconds and collecting the small organic compound. The small organic compound, in some embodiments is collected in a fraction having a maximum volume of 2 milliliters.

In other embodiments, including those listed above, the mixture of molecules is a member of a combinatorial library of small organic molecules. Preferably the combinatorial library is made by means of parallel synthesis methods and the method is performed for high throughput purification and/or quality control analysis.

Each of the limitations of the invention can encompass various embodiments of the invention. It is, therefore, anticipated that each of the limitations of the invention involving any one element or combinations of elements can be included in each method.

DETAILED DESCRIPTION OF THE INVENTION

The present invention provides new methods for the separation of small organic molecules using reverse phase HPLC with applications for the analysis and/ore preparative isolation of the separated compounds. Although the underlying principles of analytical and preparative HPLC are the same (i.e., separating mixtures into discrete components), traditionally the mode of operation has been different. The goal of analytical HPLC has been focused on obtaining optimum resolution utilizing a minimum amount of material, whereas preparative chromatography has been focused on loading the maximum quantity of material that could satisfactorily be resolved. Moreover, since isolation of a particular component is of interest in preparative chromatography, the eluant is collected after separation. This duality of operation was reasonable when the analysis or preparative isolation was for a small number of compounds, where each analysis could be customized. However, using this same approach to analyze and/or purify a large number of different compounds synthesized by parallel synthesis is too costly and time consuming. In order to maintain a high throughput operation for both analytical and preparative isolation, new faster methods of the invention have been developed where the difference between analytical and preparative approaches are only in the scale of the equipment. By appropriately scaling up the column dimensions and the flow rate, the same separation, having the same resolution, can be achieved by loading 1 to 100 mg on a preparative column as can be achieved with 1 to 10 ug loading on an analytical column.

As used herein a "method for analysis" of small organic compounds is a method in which a sample of small organic compounds is loaded on a column and performed according to the methods of the invention described herein. In the method for analysis the sample may or may not be collected. In a preferred embodiment when the analysis method is performed the sample is not collected. Preferably the method for analysis involves the step of loading less than 20 µg, and even more preferably less than 10 µg, of sample on the column.

As used herein a "method for preparative isolation" of small organic compounds is a method in which a sample of small organic compounds is loaded on a column and performed according to the methods of the invention described herein and wherein the compounds are collected in fractions as they elute from the column. Preferably the method for preparative isolation involves the step of loading less than 100 mg, and even more preferably between 1 and 100 mg, of sample on the column.

The new methods of the invention include both analytical and preparative separations and are significantly faster than prior art methods. The methods of the invention are particularly advantageous for separating components in small molecular weight combinatorial libraries as part of the quality control analysis and/or purification often conducted for such libraries. Prior to the invention each sample of certain combinatorial libraries required approximately 5–20 minutes for separation by HPLC. (Weller, et al., *Molecular Diversity*, (1997), 3:61–70) Using the method of the invention, it has been discovered, surprisingly, that the separation time per sample can be reduced to less than one minute. The time reduction significantly increases the number of samples which can be separated per unit time per instrument. At a minimum, the invention reduces the time of separation by a factor of five over prior art methods, enabling the separation of at least five times as many compounds. In preferred embodiments, the methods are more than 10 times faster than the prior art methods. Using the prior art methods which typically require a total HPLC run time of 10 minutes on fully automated equipment, approximately 2,000 samples can be separated per month. Using the methods of the present invention, which only require a run time of 1 minute, 20,000 samples can be separated in the same time period. The new methods are described in detail below.

Figure 1:
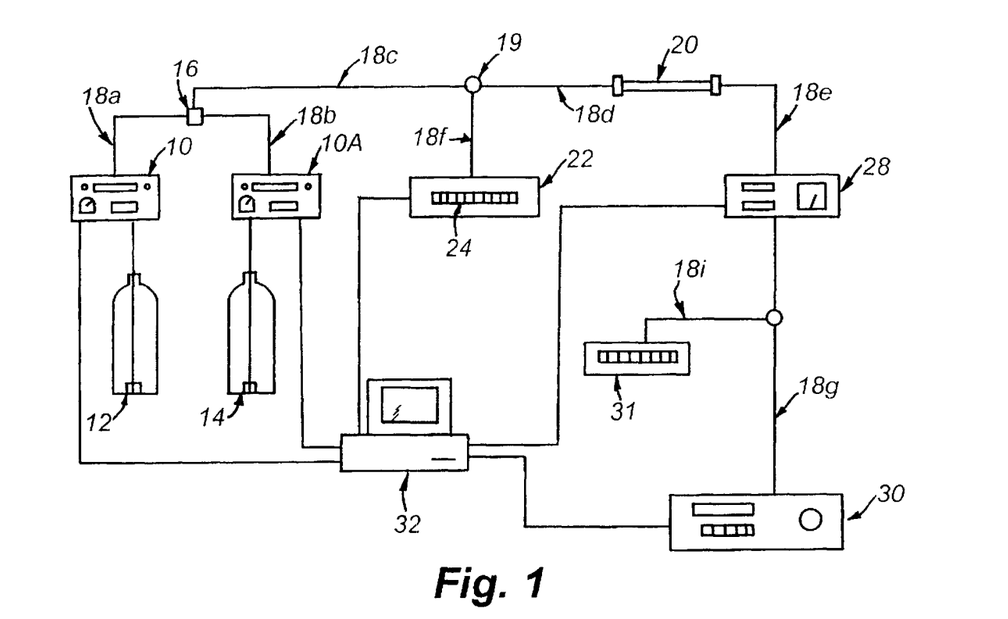
FIG. 1 is a schematic representation of the instrumentation to perform the method of the present invention.

FIG. 1 illustrates the instrumentation useful according to the general method of the invention. Two solvent reservoirs, 12 and 14, housing solvents A and B are pumped by pumps 10 and 10A through tubes 18a and 18b, respectively, into mixing chamber 16. A computer 32 controls the amount of solvent A and B which is pumped into the mixing chamber over time. Solvents A and B are mixed in the mixing chamber to form a homogenous solvent which passes through tube 18c to a high pressure valve 19 and into a column 20 containing a reverse phase packing material referred to as the stationary phase. A plurality of samples are housed within a microtitre plate 24 which rests in an auto injector 22 which is also connected to the switching valve by tubing 18f. The sample in each well of the plate 24 is transported via tubing 18f through the switching valve and then to the column through tubing 18d by automated means. Once the sample enters the column, the small organic compounds within the sample adsorb to the stationary phase with different affinities based on the hydrophobicity of the compound. After the sample is loaded the proportion of solvent A and solvent B is shifted with respect to time in order to create a gradient of solvent that is passed over the column. At certain points within the gradient, different small organic molecules are eluted from the column and carried to a detection device. The eluant is passed through a detection device such as a UV detector 28 to characterize the compounds within the eluant. In some cases the eluant is exposed to multiple detectors such as a UV detector and a mass spectrometer 30. If isolation of a particular component is of interest, the eluant from the UV detector is split into a minor portion that goes to the mass spectrometer via tube 18g and a major portion which is transferred to the fraction collector (31) through tube 18i. The equipment necessary to practice the present invention can be assembled from commercially available devices. Although some of these devices were actually designed for other functions related to HPLC analysis, they can easily be adapted to the functions described herein. For instance the 50 µl mixing chamber which is shown in a preferred embodiment for mixing eluant in the analytical setup is actually a chamber which is ordinarily used for post column derivitization purposes. Additionally, the other devices which are assembled to produce the equipment are used according to the preferred embodiment of the invention and are adjusted as described in more detail below to produce the equipment useful for practicing the method of the invention.

The methods of the invention depend in part upon the discovery that small organic molecules could be analyzed and purified on a complete gradient reverse phase HPLC by minimizing the volume of liquid applied to the column, maximizing the linear flow velocity and compressing the gradient time to produce a peak production of at least 1 peak/2 seconds. Prior to this invention, it was believed that manipulating these parameters beyond the levels described in the prior art would significantly decrease the resolution of the peaks eluting off the column to an extent that it would not be possible to obtain discrete separation of a mixture of small organic compounds. For instance, combinatorial libraries containing small organic molecules are often separated with gradient reverse phase HPLC using a run time of approximately five to twenty minutes for quality control analysis. It was believed, according to the prior art, that reducing the total run time by decreasing column volume and increasing linear flow velocity would produce an equivalent loss in resolution. Surprisingly it was discovered according to the invention that run time could be reduced by five fold over the minimum run time which has been described in the prior art with only a minimum loss in resolution, based on peak capacity, if the gradient time is also decreased. This finding indicates that the methods of the invention can produce much faster separations with minimum reduction of peak capacity than those seen in the prior art. The parameter of peak capacity is defined as the number of baseline separated peaks that will fit within the time that the gradient is changed from a low percent of solvent B to a high percent of solvent B. In order to normalize between different analyses, the peak capacity divided by the gradient time is defined as the "peak production", and expressed in units of peaks/second. Using the methods of the invention at least 1 peak/2 seconds can be resolved. Preferably 1 peak/1 second and even more preferably 1 peak/0.5 seconds are resolved using the methods of the invention. Resolution is the ability to distinguish individual compounds eluting from the column. Adequate resolution according to the invention is the ability to resolve 1 peak every 2 seconds. As used herein, this means that the peak width at baseline is on average not more than 2 seconds. A determination of resolution using a measure of baseline peak width is found in L. R. Snyder, J. J. Kirkland, J. L. Glajch, "Practical HPLC Method Development" $2^{nd}$ Edition, John Wiley & Sons, Inc., (1997).

As will be apparent from FIG. 1 and the description above, several variables will affect the peak production capacity of the method. Amongst these are (1) size of the column, (2) the packing material used in the column, (3) the use of a full gradient in a minimum volume, (4) the total volume of liquid passing over the column, and (5) the linear flow velocity. These variables should be adjusted, as further described below, to produce a rapid method having a maximum run time of one minute and a peak production of at least 1 peak/2 seconds.

In preferred embodiments, the column used according to the method of the invention is short and wide. Preferably the column has a length of less than 30 mm. A shorter column allows for a higher flow rate. With longer columns, flow rate must be reduced in order to minimize the back pressure which is created within the column. Additionally a wide column, such as a column having an internal diameter of greater than 4 mm, is preferred in order to minimize extra column band broadening associated with other parts of the instrumentation. However, a column having any width may be used according to the methods of the invention. A preferred width for analytical HPLC is between 4 and 5 mm. A preferred width for preparative isolation is between 20 and 30 mm.

The packing material used in the column is a solid support particle with reverse phase properties. Preferably, the packing material has a particle size of less than 5 $\mu$m and more preferably less than 4 $\mu$m. Such packing materials are commercially available and are well known to those of skill in the art. It is possible that improved packing materials will be developed and in such case the preferred particle size may vary depending on the improvement in the materials.

Figure 2:
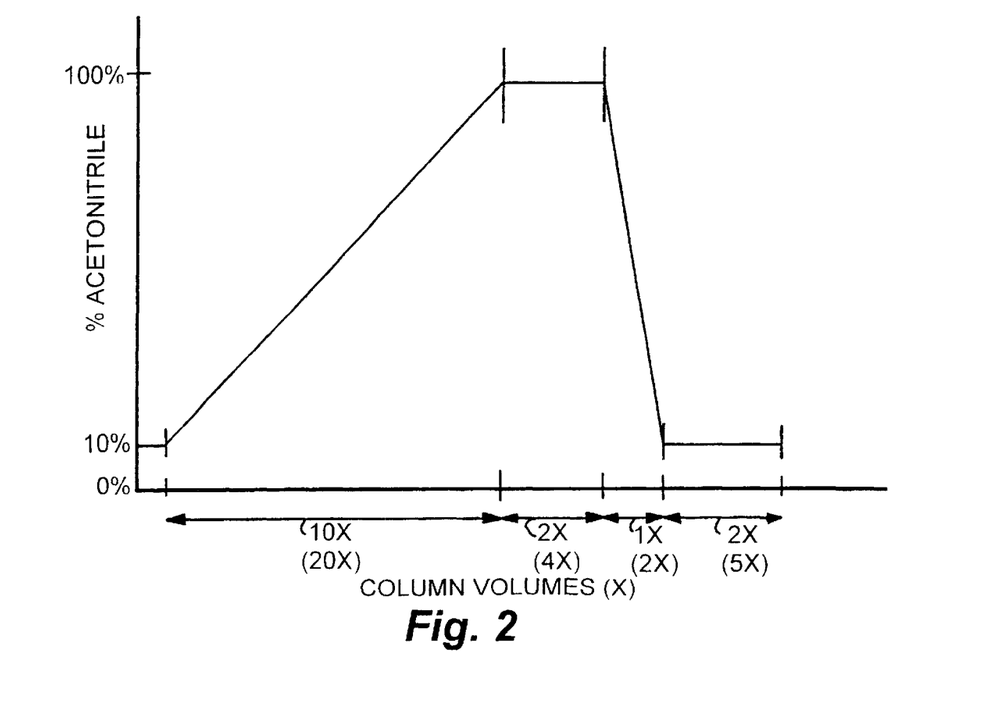
FIG. 2 is a graph depicting the composition of the mobile phase during the HPLC analysis in terms of the number of column volumes of eluant applied to the column.

The appropriate volume of solvent applied to the column is an important parameter to the method of the invention. Ordinarily, approximately 30 column volumes of solvent is applied to a column in a full gradient HPLC analysis and often more for preparative isolation. The maximum volume used according to the invention is 15 column volumes and preferably 8 column volumes to maximize speed. A graph depicting the maximum volume of liquid applied according to the methods of the invention in units of column volume is presented in FIG. 2. The volumes used in prior art methods is presented in parentheses below the volume of the invention. As shown in the figure a complete gradient is applied to the column within 10 column volumes over a time course of 20–40 seconds. Prior art gradients require 15–30 column volumes to achieve a complete gradient. A cleaning cycle of 2 column volumes of 95% acetonitrile or other elution solvent is used to flush any remaining molecules from the column over a time period of approximately 5–10 seconds. The column is then equilibrated within 1 column volume and subjected to initial solvent conditions for one column volume over a total time period of approximately 5–15 seconds.

The preferred mixing volume of the solvent is the minimum volume that permits a homogenous mixture of solvent A and solvent B. The minimum volume is achieved by utilizing a small volume mixing chamber and minimum volume of tubing. An appropriate mixing chamber for the analytical embodiment has an internal volume of less than 250 $\mu$l and preferably less than 50 $\mu$l. Although such small mixing chambers are not commercially available, 50 $\mu$l post-column reaction chambers, which are commercially available can be used as a mixing chamber. In addition to selecting a mixing chamber having a minimum size, it is preferred that the mixing chamber be static. A static mixing chamber as used herein is a chamber or column packed with beads, usually made of steel or glass. As the solvent moves over the beads, it is subjected to turbulence and caused to be mixed together.

It is important that the method of the invention be performed using a complete gradient in order to assure that all components injected on the column have been removed from the column prior to the injection of the next sample. A "complete gradient" as used herein is a gradient of solvent which begins with a low percentage of solvent B (solvent B is a non-polar solvent such as acetonitrile) and a high percentage of solvent A (solvent A is the aqueous phase). A low percentage of solvent B is preferably below 20%. The percentage of solvent A and B is shifted with time to produce a high percentage of solvent B and a low percentage of solvent A. A high percentage of solvent B is preferably above 70%.

The flow rate and the mixing volume dictate the time for the two solvents to reach the HPLC column, which in our analytical system is much less than 0.1 minutes. Using a 50 $\mu$l mixing chamber, minimal tubing, and a flow rate of 3–5 ml/min the movement of the solvent from the pumps to the column would be complete in 2–6 seconds. Another important parameter is the linear flow velocity, the velocity with which the solvent moves through the column. The linear flow velocity is dependent on the flow rate and the internal diameter of the column. Preferably the linear velocity is greater than 3 mm/sec.

An additional parameter that can be used to increase peak capacity is temperature. As demonstrated in the examples below, when the temperature of the sample through the continuous liquid path is increased over 20° C., the peak capacity is significantly increased. When combined with the high flow rates of the invention, the methods performed under high temperatures provide significant increases in peak capacity. Thus, although the methods of the invention may be performed at any temperature suitable for HPLC analysis, higher temperatures may be preferred to increase the peak capacity of the system. In some embodiments, the temperature may be a temperature greater than or equal to 20° C., 30° C., 40° C., 50° C. or 60° C. When selecting an appropriate temperature for the HPLC method, one of ordinary skill in the art will be aware that some compounds may be unstable at higher temperatures. Those of ordinary skill in the art will be able to identify those compounds which are unstable at high temperatures.

The method of the invention is useful for separating small organic compound mixtures. The mixture of compounds can include a number of small organic compounds of unknown composition having variations in hydrophobicity. The method of the invention has the capability to resolve at least 30 compounds that exhibit different hydrophobicity characteristics, as identified by the gradient composition at which each compound elutes, in one minute or less. Under conditions in which the resolution power of the method results in a peak production of 1 peak/1 second, the method of the invention has the ability to resolve approximately 60 such compounds in one minute.

Usually, the mixture of compounds includes much less than the maximum number of compounds capable of being resolved by the system. For instance, a preferred mixture of compounds includes reactants and a substantially pure product of the reactants. A mixture of compounds containing a "substantially pure product of the reactants" as used herein is a mixture containing primarily the intended product, a small amount of unreacted starting materials, as well as a few (preferably less than 5) side products in significantly lower quantity than the intended product. Such a mixture is achieved by using reactants which are only capable of producing a limited number of products under the given reaction conditions. In a preferred embodiment of the invention, the mixture of compounds is one derived from the preparation of a combinatorial library. A "combinatorial library of small organic compounds" is a collection of closely related analogs that differ from each other in one or more points of diversity and are synthesized by organic techniques using multi-step processes. Combinatorial libraries include a vast number of small organic compounds, some of which may have important biological activity.

One type of combinatorial library, which is preferred according to the invention, is prepared by means of parallel synthesis methods to produce a compound array. A "compound array" as used herein is a collection of compounds identifiable by their spatial addresses in Cartesian coordinates and arranged such that each compound has a common molecular core and one or more variable structural diversity elements. The compounds in such a compound array are produced in parallel in separate reaction vessels, with each compound identified and tracked by its spatial address. Regardless of the relative amount of starting materials and products that are in each reaction vessel after reaction, the method of the invention can be used to analyze the extent of reaction and/or isolate the components. Examples of parallel synthesis mixtures and parallel synthesis methods are provided in U.S. Ser. No. 08/177,497 filed Jan. 5, 1994 and its corresponding PCT published patent application WO95/18972, published Jul. 13, 1995 and U.S. Pat. No. 5,712,171 granted Jan. 27, 1998 and its corresponding PCT published patent application WO96/22529.

Once a series of small organic compound mixtures are developed, the mixtures can be separated and analyzed to determine the product formed and the extent of reaction. Each mixture of compounds represents a separate sample that is injected onto an HPLC column. As shown in FIG. 1 each sample is held within a well of a microtitre plate 24 in an autosampler 22. The samples are loaded and injected manually or automatically using equipment controlled by a computer 32. The automatic loading and injection of the samples is preferred because it enables the continuous loading of samples at a rate which will not limit the overall process of analysis.

Prior to loading the sample on the column the column is conditioned by flowing through it the intended mobile phase. As discussed above, the column is packed with a non-polar stationary phase on solid support particles, and can be obtained from a variety of commercial sources. HPLC columns can be obtained from a variety of commercial sources such as MACMOD (Chaddsford, Pa.). Once the column is conditioned, the system is initiated by the injection of the sample. As the small organic compounds contact the non-polar packing material each molecule is adsorbed to the packing material. The affinity with which each compound adsorbs to the packing material is dependent on the hydrophobicity of the individual compound. The injection of the sample defines time zero for the run.

A gradient is applied to the column immediately after the injection of the sample in order to elute the compounds bound therein in distinct fractions. A gradient HPLC system includes two reservoirs, 12 and 14, each containing a different polarity solvent which are pumped through a mixing chamber 16 and over the column 20 by means of a pump. In a preferred embodiment, solvent flow is maintained by a non-pulsating HPLC pump such as that available as part of a Shimadzu (Columbia, Md.) HPLC system. A full gradient from 15% to 95% of acetonitrile is then applied to the column. The compounds in the mixture injected on the column which are polar have a greater affinity for the initial composition of the eluant than the stationary phase and are thus eluted more rapidly than the more non-polar compounds which have a greater affinity for the hydrophobic stationary phase. Solvents typically used for gradients in reversed phase HPLC generally include acetonitrile, methanol, isopropanol and propanol. Modifiers are typically added to the mobile phase, primarily to buffer the pH to a certain narrow range, and include a variety of acids and bases such as phosphoric acid, perfluorinated carboxylic acids and amines.

An HPLC compatible detector is used to detect the presence of small organic compounds as they are eluted from the column. A compatible detector is one which is capable of detecting a signal from a compound in an eluant and which produces a signal to indicate the presence of that compound. The detector should allow data acquisition at a rate of greater than 10 points per second and preferably greater than 20 points per second. HPLC compatible detectors include, but are not limited to, fluorescent, electrochemical, IR, NMR, chemiluminescent, UV and mass spectrometry. Preferably the HPLC compatible detector is a UV detector 28, since commercially available UV detectors are capable of achieving the required data acquisition rate when the settings are adjusted to achieve maximal values. Furthermore, UV detectors are generally applicable to a large and diverse number of chemical clauses and a large variety of mobile phases.

In some cases, the HPLC compatible detector is both a UV detector 28 and a mass spectrometer 30. The use of both a UV detector and a mass spectrometer is preferred because it allows the methods of the invention to achieve, both purity (by UV) and structural (by MS) information for each separated and detected component being eluted from the column. Moreover, the mass spectrometer can be used as a high specificity multi-dimensional detector to provide general information on a class of compounds or specific information on a particular compound. These beneficial properties coupled with the inherent high sensitivity of the mass spectrometer make it one of the most desirable detectors to be coupled with the separation power of HPLC.

In the aspect of the invention described above the method may be used for analysis, such as quality control analysis and/or for preparative isolation of at least one component of a mixture of compounds. In this aspect of the invention one or more compounds may be collected after separation on the column in distinct fractions. The HPLC compatible detector is used to identify the presence of a compound in each fraction and the fractions are separated into an acceptable container such as a tube or a well of a microtitre plate.

In another aspect the invention is a rapid high performance liquid chromatography method for the preparative isolation of a concentrated fraction of a small organic compound from a mixture of compounds. Each of the parameters described above in relation to the method of separation are also applicable to this aspect of the invention. The method in this aspect of the invention differs, however, from the above method in that the separation of molecules is performed only for the purpose of separating compounds in a mixture into distinct fractions and the compounds are collected for future analysis or use. The method is performed as described above except that the elution permits resolution with a peak production of at least 1 peak/4 seconds. In some embodiments the elution permits resolution with a peak production of at least 1 peak/2 seconds.

Preferably the compounds are collected in fractions having a volume of 2 milliliters or less. The methods of the invention accomplish the separation of compounds in such a short time that the total volume that each compound elutes in 2 milliliters or less. This is advantageous because the compound of interest is present in a fairly concentrated form as opposed to the prior art methods where the compound of interest is often eluted in a minimum volume of 4 milliliters.

As described above, many variations on these particular examples are possible and, therefore, the examples are merely illustrative and not limiting of the present invention.

EXAMPLES

Example 1

Gradient Reverse Phase HPLC Analysis of Standard Mixtures of Small Organic Molecules Equipment: All analytical separations were performed on a Shimadzu (Columbia, Md.) HPLC System consisting of two LC-10AS pumps, a SIL-10A autosampler, a SCL-10A system controller and a SPD-10A UV-detector. The system was modified for high performance application in the following manner. A low volume static mixer from Supelco (Bellefonte, Pa.) with a 250 ul cartridge was used for fast and efficient high pressure mixing of the eluents. In combination with the short 30 mm columns a 50 ul mixing cartridge was used to further minimize gradient delay. The original bypass of the Shimadzu autoinjector was removed to eliminate band broadening effects. Injection was performed in the partially filled loop mode, injecting between 1 and 5 ul in a 50 ul loop. Connections between injector, column and detector were made with 0.007" tubing and the length kept at a minimum to prevent extra column band broadening. The original flow-cell of the UV detector was replaced with a semi-micro version, having a path length of 5 mm and a smaller total volume of 2.5 ul. The detector response was set to 1 to allow for detection of rapidly eluting, narrow peaks. Data acquisition was performed by the Chromperfect software from Justice Innovations (Palo Alto, Calif.) at a rate of 20 points/second.

Chemicals: Water and acetonitrile were HPLC grade, dimethylsulfoxide was A.C.S. grade from Baker (Philipsburg, N.J.). All other chemicals were the highest available purity grade from Aldrich (Milwaukee, Wis.). The HPLC eluents were prepared by adding 0.1% (v/v) trifluoroacetic acid to water (solvent A) and acetonitrile (solvent B).

HPLC Columns: The Zorbax SB-C8 columns (50 mm×4.6 mm and 30 mm×4.6 mm both packed with 3.5 $\mu$m particles; 150 mm×4.6 mm packed with 5 $\mu$m particles) were obtained from MACMOD (Chaddsford, Pa.). The Prontosil C18-SH columns (50 mm×4.6 mm, 3 $\mu$m particles) was a gift from Bischoff Analysentechnik (Leonberg, Germany).

Figure 3:
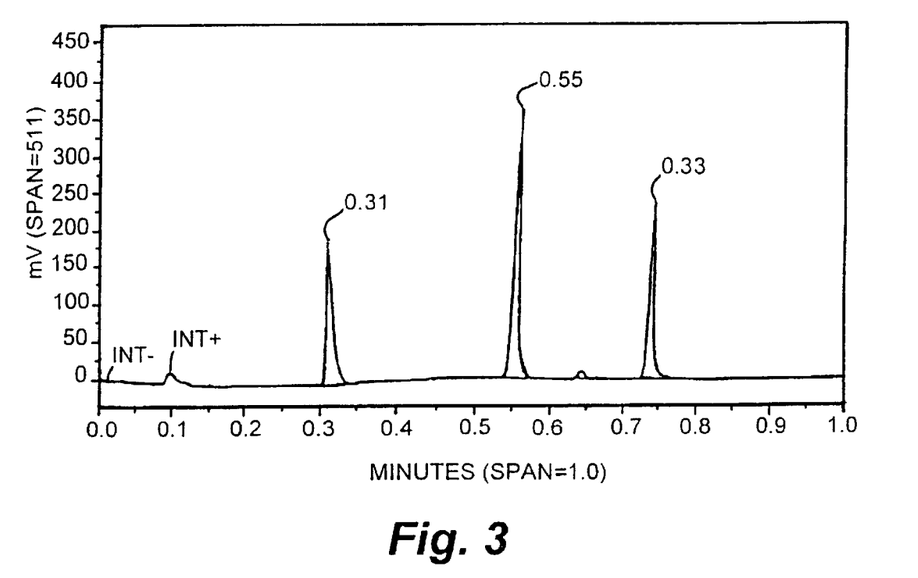
FIG. 3 is a chromatogram of a test mixture obtained using the method of the present invention with less than 1 minute total analysis time.

An example of a large difference in compound hydrophobicity is represented by our standard test mixture, which consists of the following components: acetamidophenol, 2-hydroxydibenzofuran and t-butylphenoxybenzaldehyde. In a reverse phase HPLC separation, the acetamidophenol elutes during the initial part of the gradient, the 2-hydroxydibenzofuran elutes in the middle of the gradient and the t-butylphenoxybenzaldehyde elutes at the end of the gradient. A mixture of the three compounds was prepared in dimethylsulfoxide (DMSO). The mixture was then subjected to HPLC analysis according to the methods of the invention under the condition described above:

The test mixture was first analyzed with a column packed with reverse phase silica having 3.5 $\mu$m particle size, at a flow rate of 3 ml/min in addition to each of the above conditions. The compounds were eluted with a gradient of 15–95% acetonitrile applied to the column in 0.7 min with 10 second hold and 5 second equilibration time. The results are shown in FIG. 3. Three major peaks representing each of the three components of the test mixture were resolved in less than 1 minute. Based on the baseline peak width of the middle peak, approximately 60 compounds with varying hydrophobicities could be baseline resolved with this method.

Figure 4:
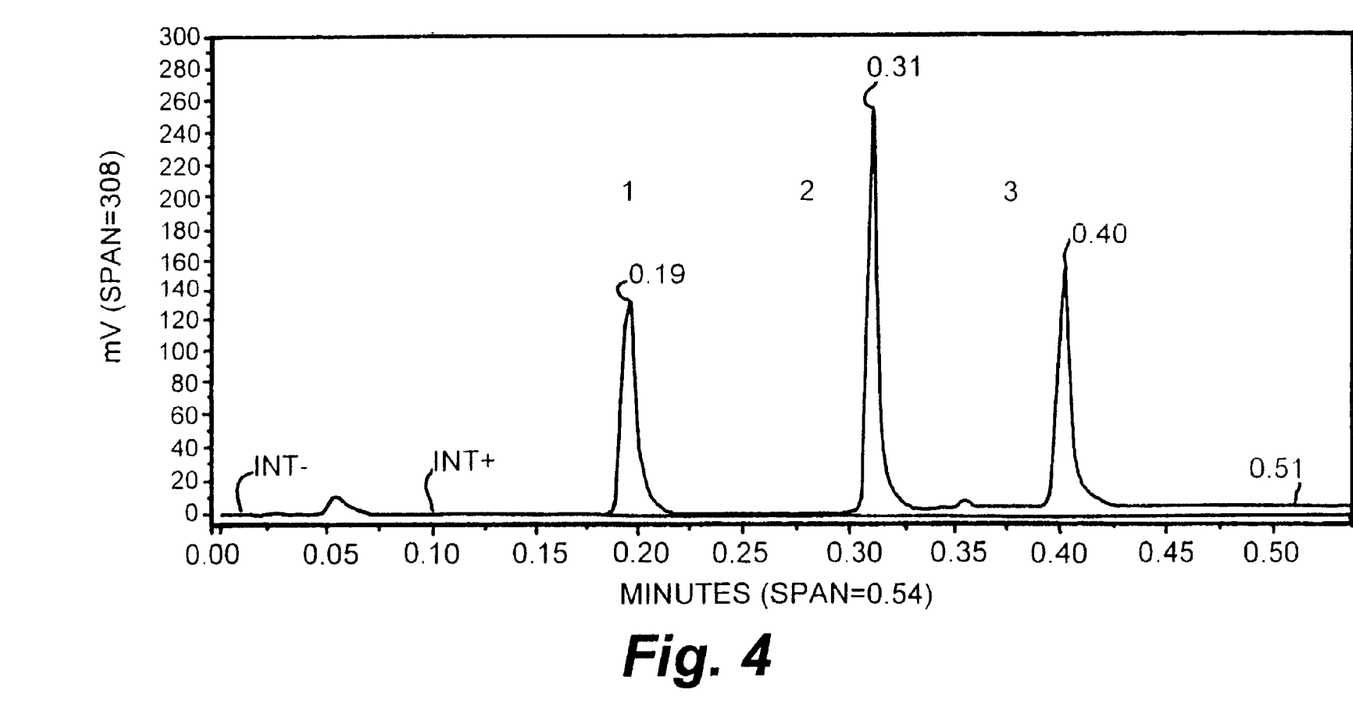
FIG. 4 is a chromatogram of a test mixture obtained using the method of the present invention with less than ½ minute total analysis time.

The same mixture of compounds was analyzed with a column packed with reverse phase silica having 3.5 $\mu$m particle size, at a flow rate of 5 ml/min in addition to each of the above conditions. The molecule were, again, eluted with a gradient of 15–95% acetonitrile applied to the column in 0.3 min with a 10 second hold and 5 second equilibration time. The results are shown in FIG. 4. Once again based on the width of the middle peak, approximately 30 compounds of varying hydrophobicities could be baseline resolved with this 30 second method.

Example 2

Figure 5:
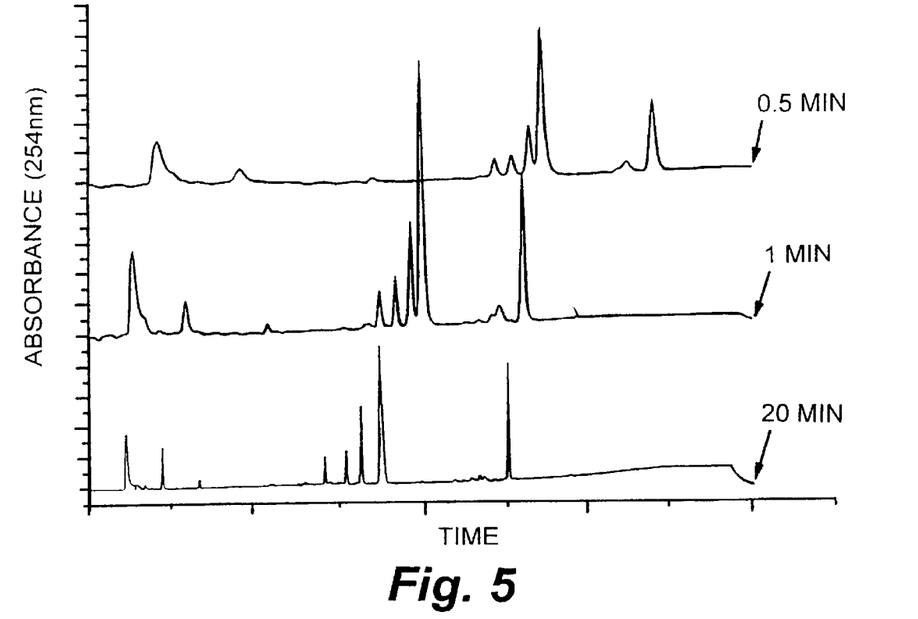
FIG. 5 is a comparison of the chromatograms obtained for a sample synthesized by parallel synthesis using a 20 minute, a 1 minute, and a 30 second analysis.
Figure 6:
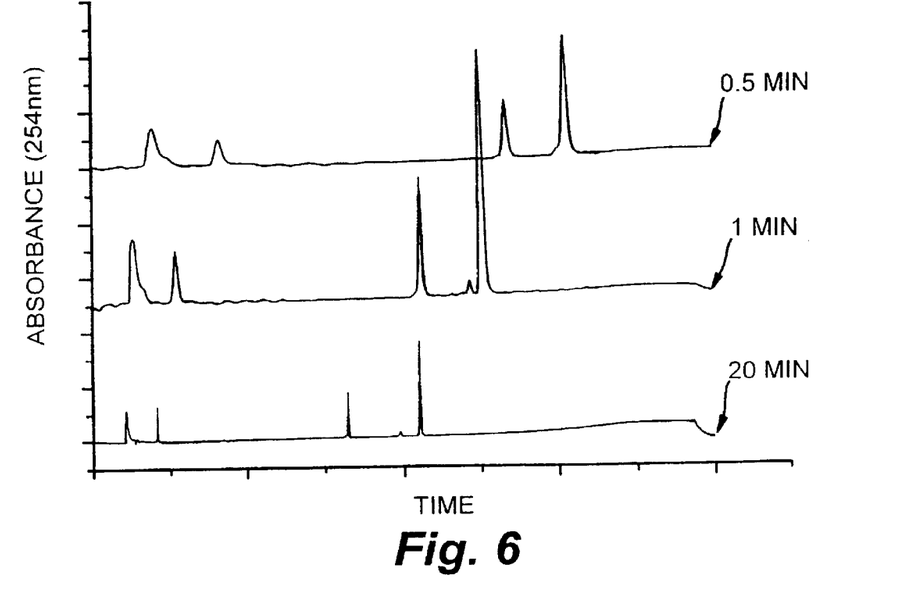
FIG. 6 is another example of a comparison of the chromatograms obtained for a sample synthesized by parallel synthesis using a 20 minute, a 1 minute, and a 30 second analysis.

Gradient Reverse Phase HPLC Analysis of Combinatorial Library Samples Obtained by Parallel Synthesis One sample from two different combinatorial libraries prepared by parallel synthesis by methods such as those disclosed in U.S. Ser. No. 08/177,497, filed Jan. 5, 1994 and its corresponding PCT published patent application WO95/18972, published Jul. 13, 1995 and U.S. Pat. No. 5,712,171 granted Jan. 27, 1998 and its corresponding PCT published patent application WO96/22529 were chosen for analysis using the methods described in Example 1. The results for sample A1990702D9 analyzed using a traditional 20 minute analysis are compared to those obtained from the 1 minute and 30 second analysis in FIG. 5. The 20 minute method used a Zorbax SB-C8 (150×4.6 mm) packed with 5 μm particles and a full gradient (15%–95% solvent B) at 15 ml/min. Although the peak capacity is less for the shorter analyses, the resolution is more than adequate to determine purity, even in such a complex sample which would be the worst case scenario. Similarly, the results for sample AQ130QC48H5 using the 20 minute, 1 minute and 30 second analyses are given in FIG. 6. Once again, the 1 minute method provides the same purity information as the longer 20 minute analysis. Moreover, the 30 second analysis provides similar information. Although the small peak between the two major ones is partially merged with the major component, there is still adequate resolution to indicate the presence of the minor component. The foregoing written specification is considered to be sufficient to enable one skilled in the art to practice the invention. The present invention is not to be limited in scope by the disclosed embodiments, since these embodiments are intended merely as illustrative of particular embodiments of the invention as enabled herein and any methods that are functionally equivalent are within the scope of the invention. Indeed, various modifications of the invention in addition to those shown and described herein will become apparent to those skilled in the art from the foregoing description and fall within the scope of the appended claims.

Example 3

Figure 7:
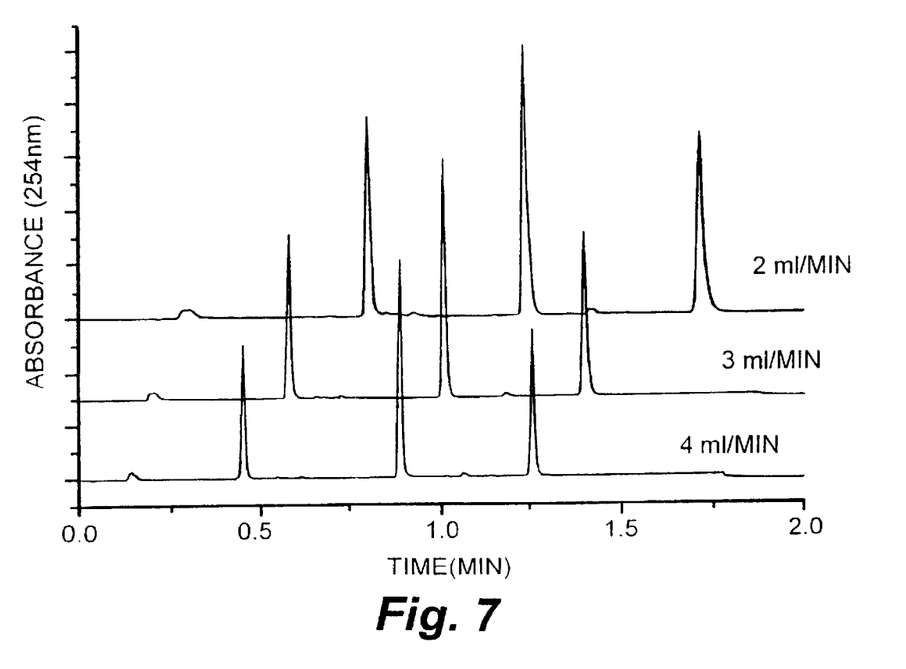
FIG. 7 is a series of chromatograms obtained using the method of the present invention in order to determine peak capacity obtained with various flow rates using a 50×4.6 m, 3 μm Prontosil C18-SH column: (7A) flow rate of 2 ml/min; (7B) flow rate of 3 ml/min; and (7C) flow rate of 4 ml/min.

Effect of Flow Rate on the Rapid Gradient Reverse Phase HPLC Analysis of the Invention In order to determine the effect of flow rate on the rapid analysis methods of the invention, the method was performed using various flow rates ranging from 2 to 4 ml/min. The data is shown in FIG. 7. In the case of the very steep 1 minute gradient, an increase in the flow rate from 2 ml/min (resulting in a gradient volume of 2.4 column volumes) to 4 ml/min (4.8 column volume) increases the peak capacity from 29 to 48. The larger gradient volume achieved by increasing the flow rate also lowers the total analysis time as indicated by the elution of the last peak. The peak production rate in this case almost doubles with the flow rate from 0.47 to 0.8 peak/sec. The linear flow rate at 4 ml/min was 6.4 mm/second and the back pressure was about 250 bar which is acceptable for a routine application. Thus, columns can be run at very high linear flow rates with steep gradients in order to obtain a high peak capacity and peak production rate.

Example 4

Gradient Reverse Phase Preparative HPLC Analysis of Standard Mixture of Small Organic Molecules Equipment: Preparative separations were performed with a system of two Rainin Dynamax SD-1 pumps (Woburn, Mass.), a Gilson-215 (Madison, Wis.) configured as both an autosampler and fraction collector, a Shimadzu (Columbia, Md.) SPD-10A UV detector with a preparative cell. Injection was performed in the partially filled loop mode injecting 250 ul in a 5 ml loop. Detection was at 254 nm and the detector response was set to 1 to allow for detection of rapidly eluting, narrow peaks. Data acquisition was performed by Unipoint software from Gilson (Madison, Wis.).

Chemicals: Water and acetonitrile were HPLC grade, dimethylsulfoxide was A.C.S. grade from Baker (Philipsburg, N.J.). All other chemicals were the highest available purity grade from Aldrich (Milwaukee, Wis.). The HPLC eluents were prepared by adding 0.1% (v/v) trifluoroacetic acid to water (solvent A) and acetonitrile (solvent B).

HPLC Columns: YMC ODS-A C18, 20 mm×50 mm packed with 5 um particles obtained from YMC (Wilmington, N.C.).

Figure 8:
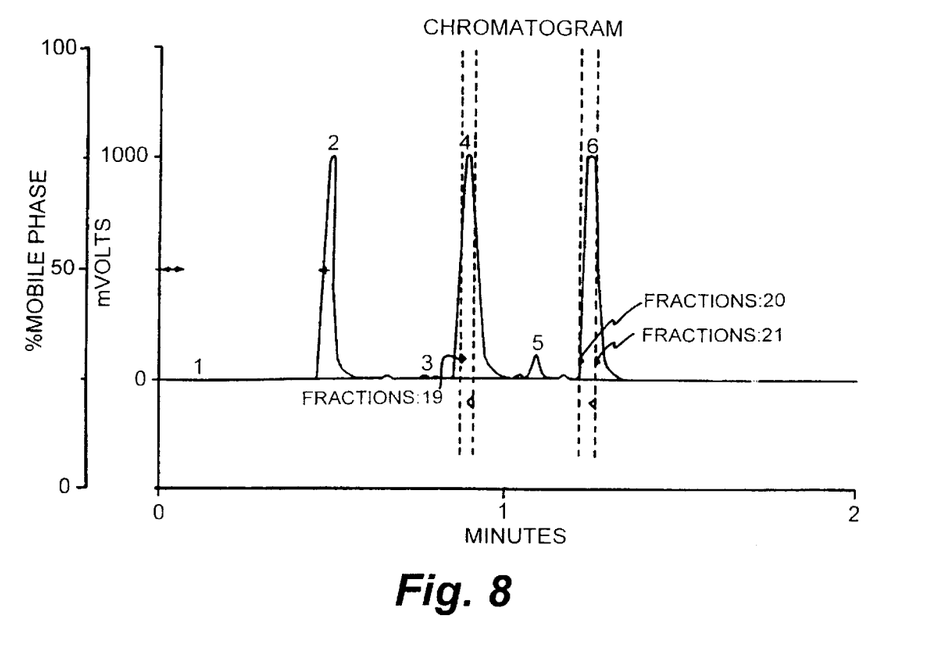
FIG. 8 is a chromatogram obtained from a preparative isolation of 10 mg of each of the three standard compounds using a 20 mm×50 mm column packed with 5 um particles and a flow rate of 80 ml/min.

The standard test mixture of acetamidophenol, 2-hydroxydibenzofuran, and t-butylphenoxybenzaldehyde was prepared at 40 mg/ml of each component in DMSO. The mixture was then subjected to preparative HPLC analysis. The flow rate of the mobile phase was 80 ml/min and the compounds were eluted with a gradient of 10%–95% acetonitrile applied to the column in 1 minute with a 20 second hold and a 40 second equilibration time. The fraction collector was set to collect the second and third peak. The results are shown in FIG. 8. Based on the baseline peak width, approximately 30 compounds with varying hydrophobicities could be resolved and collected with this method.

Example 5

Figure 9:
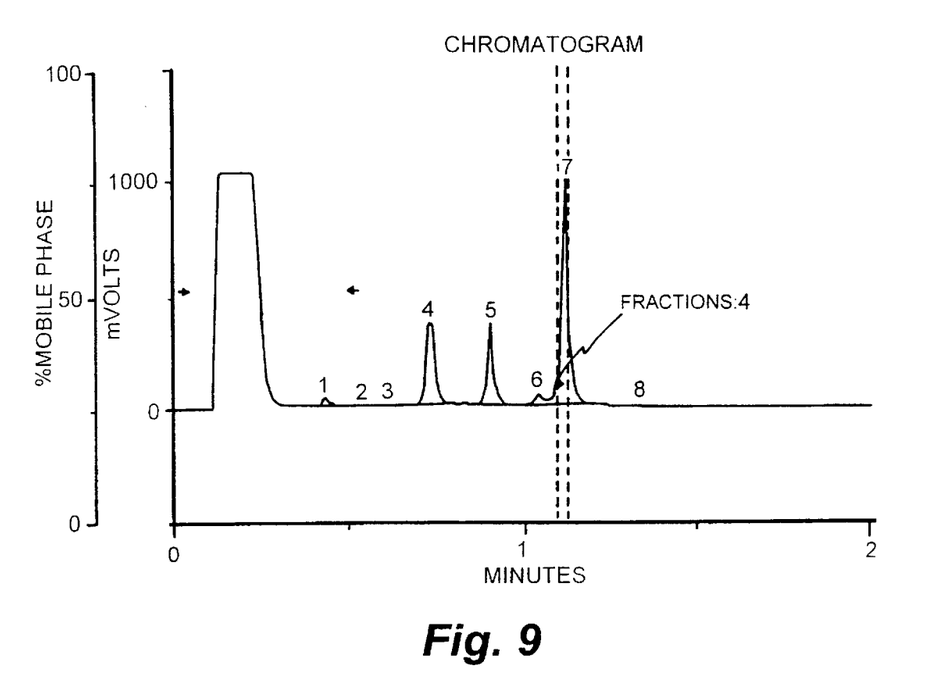
FIG. 9 is a chromatogram obtained from a preparative isolation of approximately 5 mg of a mixture prepared by parallel synthesis using the conditions identified in FIG. 8.

Gradient Reverse Phase Preparative HPLC Analysis of a Combinatorial Library Sample One sample from a combinatorial library prepared by parallel synthesis by methods such as those disclosed in U.S. Ser. No. 08/177,497, filed Jan. 5, 1994 and its corresponding PCT published patent application WO95/18972, published Jul. 13, 1995 and U.S. Pat. No. 5,712,171 granted Jan. 27, 1998 and its corresponding PCT published patent application WO96/22529 were chosen for analysis using the method described in Example 4. However, the detection was at 217 nm and 400 ul of a 30 mM solution of the sample was injected. The fraction collector was set to collect the expected product peak, which was identified as the last peak in the chromatogram. The results of sample A1990703D9 are shown in FIG. 9.

Example 6

Effects of Temperature on Rapid Gradient Reverse Phase HPLC Analysis

In order to determine the effect of temperature on the rapid analysis methods of the invention, the method was performed using various temperatures ranging from 20° C. to 60° C. under conditions such as different flow rates. The data is presented in Table I. As shown in the table, the peak capacity increases significantly when the temperature is raised from 20 to 60° C. and this increase in peak capacity is even more pronounced when the system is run at high flow rates. As shown in the table, the peak capacity of a sample run on a 30 mm column at 4 ml/min using a 1 minute method with a 0.75 minute gradient, increased from 44 at 25° C. to 55 at 60° C. This correlates to a 25% increased based on a corresponding decrease in peak width. In a similar experiment in which the flow rate and temperature are increased from 4 ml/minute to 5 ml/minute and from 25° C. to 60° C. respectively, the peak capacity increases from 44 to 60, which is a 35% increase. In addition to the changes in peak capacity, the eluent viscosity is decreased at higher temperatures. Faster flow rates at comparable pressure drops may also be accomplished at higher temperatures. For instance, a decrease in pressure of 50% was observed when the temperature was raised from 20 to 60° C. Additionally, a 5–10% increase in velocity of eluent was observed, indicated by a decrease in retention time of the compound.

TABLE 2

| peak-capacity | 4.6 × 30 mm column 4 ml/min 25 C. | 5 ml/min 25 C. | 4 ml/min 60 C. | 6 ml/min 60 C. |
|---|---|---|---|---|
| 1.00 minute method 0.75 min gradient | 44 | 47 | 55 | 60 |
| 0.75 minute method 0.50 min gradient | 37 | 38 | 44 | 48 |
| 0.50 minute method 0.35 min gradient | 29 | 30 | 34 | 39 |
| peak-capacity | 4.6 × 50 mm column 4 ml/min 20 C. | | 4 ml/min 60 C. | 6 ml/min 60 C. |
| 1.00 minute method 0.75 min gradient | 37 | | 53 | 59 |
| 0.75 minute method 0.50 min gradient | | | | 46 |

During the experimentation concerning the effects of temperature, it was discovered that the existing equipment could not effectively carry out the appropriate temperature change without some modification. Initially a column heater jacket was used in order to regulate the temperature. The column is immersed in a circulating liquid which is temperature controlled. The eluents were brought to the desired temperature through heat exchange capillaries that were immersed in a system regulated by a thermostat. It was found, however, that the temperature of the eluent dropped from approximately 50° C. to about 28° C. between the mixing device and the column at the high flow rates required for the rapid HPLC analysis of the invention. A modified version of the equipment was arranged by immersing a manual injector valve together with the heat exchanger and the column in a water bath of the desired temperature for the experimental condition. This modification to the equipment provided a homogenous temperature distribution throughout the liquid path and enabled the characterization of temperature effects described above. Those of ordinary skill in the art will be able to modify the existing equipment to accomplish these effects based on this teaching.

We claim:

1. An improved rapid method for the separation of small organic compounds in a mixture of compounds by applying the mixture of compounds to a reverse phase column (20) in a gradient high performance liquid chromatography system, applying a complete gradient to the column (20) in a maximum volume; and causing each small organic compound within the mixture of compounds to elute in a distinct fraction from the column (20), and wherein the maximum volume is 10×column volume, and eluting each small organic compound such that the elution permits resolution with a peak production of at least 1 peak/2 seconds.

2. The method of claim 1, further comprising the step of detecting at least one of the compounds as it elutes from the column (20).

3. The method of claim 2, wherein the method is a method for analysis of at least one compound in the mixture of compounds.

4. The method of claim 1, further comprising the step of collecting at least one of the compounds in a distinct fraction as it elutes from the column (20).

5. The method of claim 4, wherein the method is a method for preparative isolation of at least one compound in the mixture of compounds.

6. The method of claim 4, wherein the at least one compound is collected in a fraction having a volume of 2 milliliters or less.

7. The method of claim 1, wherein the mixture of molecules includes reactants and a substantially pure product of the reactants.

8. The method of claim 1, wherein the column (20) is less than or equal to 30 mm in length.

9. The method of claim 1, wherein the column (20) has a packing material which has an average diameter of less than 5 microns.

10. The method of claim 1, wherein the peak production is at least 1 peak/1 second.

11. The method of claim 1, wherein the peak production is at least 1 peak/0.5 seconds.

12. The method of claim 1, wherein a total volume of liquid applied to the column is less than 15×column (20) volumes.

13. The method of claim 1, further comprising a cleaning volume having a maximum of 2×column volume.

14. The method of claim 1, further comprising an equilibration volume having a maximum of 1×column volume.

15. The method of claim 1, wherein the mixture of compounds is applied to the column (20) at a first time point and wherein all compounds are eluted within a time period of less than one minute from the first time point.

16. The method of claim 15, wherein all compounds are eluted within a time period of less than 30 seconds.

17. The method of claim 15, wherein all compounds are eluted within a time period of less than 20 seconds.

18. The method of claim 1, wherein the mixture of molecules is a member of a combinatorial library of small organic molecules.

19. The method of claim 18, wherein the combinatorial library is made by means of parallel synthesis methods.

20. The method of claim 1, wherein the column has a linear velocity of at least 3 mm/sec.

21. The method of claim 1, wherein the method is a method for analysis of at least one compound in the mixture of compounds.

22. The method of claim 1, wherein the method is a method for preparative isolation of at least one compound in the mixture of compounds.

23. An improved rapid high performance liquid chromatography method for the preparative isolation of a concentrated fraction of a small organic compound from a mixture of compounds by applying the mixture of compounds to a reverse phase column (20) in a gradient high performance liquid chromatography system, applying a complete gradient to the column (20) in a maximum volume; and causing the small organic compound to elute in a distinct fraction, separate from the other molecules, from the column (20), and collecting the small organic compound, and, wherein the maximum volume is 10×column volume, and eluting the small organic compound such that the elution permits resolution with a peak production of at least 1 peak/4 seconds.

24. The method of claim 23, wherein the mixture of molecules includes reactants and a substantially pure product of the reactants.

25. The method of claim 23, wherein the column (20) is 20–30 mm in length.

26. The method of claim 23, wherein the column (20) has a packing material which has an average diameter of less than 5 microns.

27. The method of claim 23, wherein a total volume of liquid applied to the column (20) is less than 15×column volumes.

28. The method of claim 23, further comprising a cleaning volume having a maximum of 2×column volume.

29. The method of claim 23, further comprising an equilibration volume having a maximum of 1×column volume.

30. The method of claim 23, wherein all compounds are eluted within a time period of less than 60 seconds.

31. The method of claim 23, wherein the mixture of molecules is a member of a combinatorial library of small organic molecules.

32. The method of claim 31, wherein the combinatorial library is made by means of parallel synthesis methods.

33. The method of claim 23, wherein the column (20) has a linear velocity of at least 3 mm/sec.

34. The method of claim 23, wherein the small organic compound is collected in a fraction having a maximum volume of 2 milliliters.

* * * * *